United States Patent [19]

Hugues et al.

[11] Patent Number: 5,302,775
[45] Date of Patent: Apr. 12, 1994

[54] PROCESS AND APPARATUS FOR THE ENTRAINED BED CATALYTIC CONVERSION OF A CHARGE CONTAINING AN OXYGEN COMPOUND

[75] Inventors: Francois Hugues, Vernaison; Daniel Vuillemot, Saint Genis Laval; Jean Pierre Burzynski, Sainte Foy les Lyon; Pierre Galtier, Vienne; Thierry Gauthier, Saint Genis Laval, all of France

[73] Assignee: Institut Francais du Petrole, Rueil Malmaison, France

[21] Appl. No.: 831,245

[22] Filed: Feb. 7, 1992

[30] Foreign Application Priority Data

Feb. 7, 1991 [FR] France .................. 91 01519

[51] Int. Cl.5 .................. C07C 1/20
[52] U.S. Cl. .................. 585/639; 585/638; 585/640; 585/921; 585/922
[58] Field of Search .............. 585/639, 640, 638, 921, 585/922

[56] References Cited

U.S. PATENT DOCUMENTS 4,197,418 4/1980 Lee et al. .
4,229,608 10/1980 Chen et al. .................. 585/640
5,129,930 7/1992 Gauthier et al. .................. 55/394
5,186,836 2/1993 Gauthier et al. .................. 210/512.1

FOREIGN PATENT DOCUMENTS 0091751 10/1983 European Pat. Off. ............ 585/640
0096996 12/1983 European Pat. Off. ............ 585/640

Primary Examiner—Asok Pal
Attorney, Agent, or Firm—Millen, White, Zelano, & Branigan

[57] ABSTRACT

Process for the catalytic conversion of a charge incorporating at least one oxygen compound such as methanol, into olefinic hydrocarbons having 2 to 4 carbon atoms. Conversion takes place in a reactor (100), into which the charge is introduced by the pipe (20), the catalytic solid by the pipe (30) and the solid entrainment gas by the pipe (40), the reactor being connected by a pipe (1) to a co-current cyclone separator (S) making it possible to separate a solid phase from a gaseous phase containing the conversion products, which is recovered by the pipe (4). The solid phase is fed by the pipe (9) to a regenerator (R), in which the catalytic particles are at least partly regenerated before being returned by the pipe (80), connected to the pipe (30), to the reactor (100).

16 Claims, 4 Drawing Sheets

FIG.2A
FIG.2B
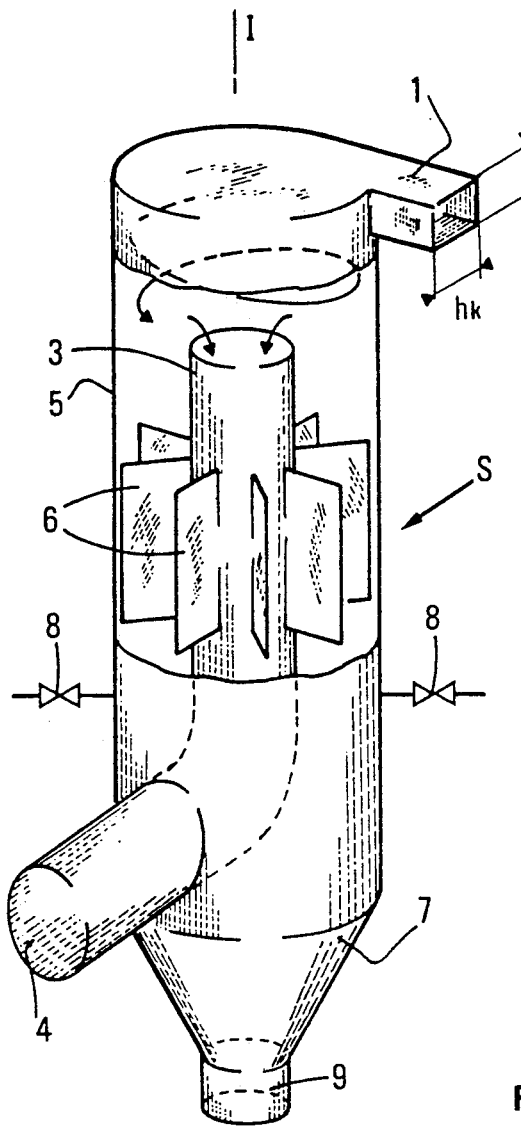
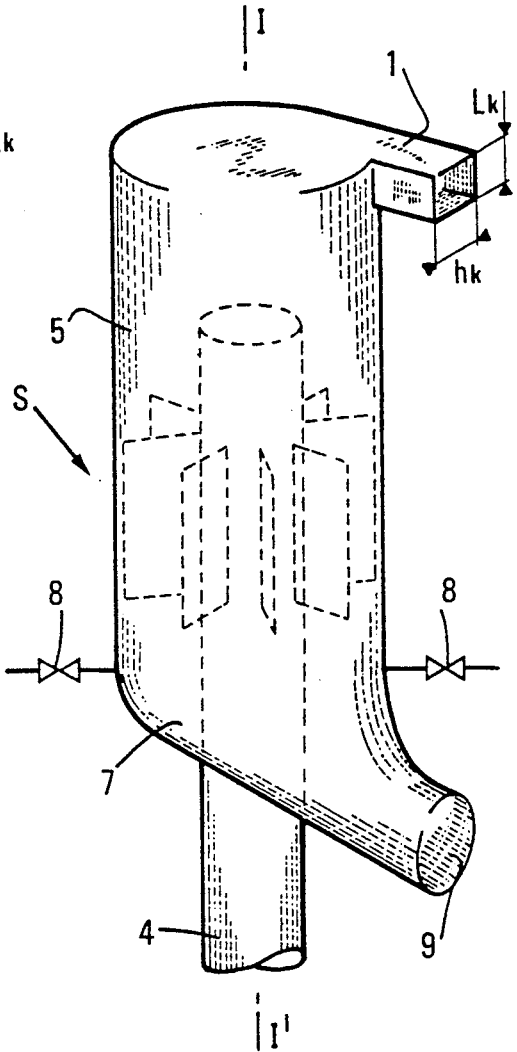
FIG.1
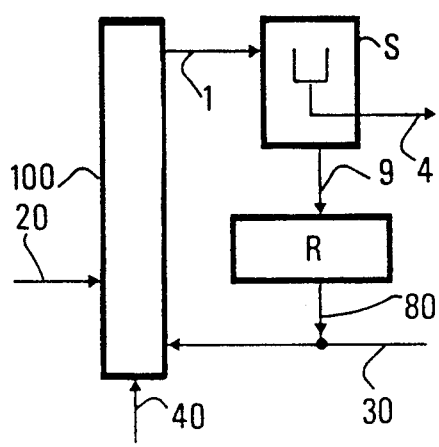

PROCESS AND APPARATUS FOR THE ENTRAINED BED CATALYTIC CONVERSION OF A CHARGE CONTAINING AN OXYGEN COMPOUND

BACKGROUND OF THE INVENTION

The invention relates to a process for the entrained bed catalytic conversion of a charge incorporating at least one oxygen or oxygen-containing compound and more specifically at least one alcohol, such as methanol and/or at least one ether oxide, such as dimethyl ether and an apparatus for performing this process incorporating at least one co-current cyclone separator permitting the very rapid separation of the solid particles and the gases.

This process is more particularly applied to the production of olefinic hydrocarbons, particularly for petrochemical uses and largely constituted by compounds having 2 to 4 carbon atoms in their molecule, in the presence of a catalyst, such as a zeolite, circulating in an entrained bed reactor. A particular use given in exemplified manner here is the catalytic conversion of methanol into ethylene and/or propylene-rich hydrocarbons. The technical background is illustrated by U.S. Pat. No. 4,197,418.

One of the essential factors in the selective production of light olefins and more particularly ethylene and/or propylene by conversion of methanol is controlling the contact time between the charge and the catalyst. This contact between the charge and the catalyst must be both short and uniform (or regular) in time, which imposes a contacting uniformity and speed between the catalyst grains and the gaseous or liquid charge. It is therefore important to more particularly control the charge quantity introduced in conjunction with the catalyst quantity with which it comes into contact, while keeping constant the contact time between the charge and the catalyst in order to bring about the optimum selectivity in the desired ethylene compound or compounds. In the absence of such a control, the tendency of the reaction is to lead to a wide range of saturated and unsaturated hydrocarbons generally extending from methane to hydrocarbons having up to or more than 10 carbon atoms in their molecule and such as those conventionally constituting the naphtha cut.

In the methanol conversion processes using the entrained bed procedure described in the prior art, there is usually an insistence on the importance of optimizing and controlling the contact time between the catalytic particles and the charge. As is e.g. stated in U.S. Pat. No. 4,229,608, this contact time must be relatively short. However, no reference is made to the use of a separation system appropriate for allowing an effective, rapid separation of the solid particles and the gases containing the reaction products.

The association of well chosen operating conditions and an ultra-fast separation of the catalytic particles and the gaseous products including the conversion products in particular makes it possible to significantly improve the selectivity with respect to the desired ethylene compound or compounds, which was not the case in the prior art, such as e.g. that described in U.S. Pat. No. 4,046,825.

SUMMARY OF THE INVENTION

More specifically, the present invention relates to a process for the catalytic conversion of a charge containing at least one oxygen compound into olefinic hydrocarbons rich in compounds having 2 to 4 carbon atoms in their molecule, comprising the entrained bed conversion of said charge, in an elongated conversion reaction zone, under appropriate conditions and in the presence of a catalyst in the form of solid particles, said process having a stage of supplying, to a zone located in the vicinity of a first end of said reaction zone, at least one solid in the form of particles containing catalytic particles and at least one entrainment fluid, an introduction stage and, in the case of an at least partly liquid charge the spraying of said charge into an introduction zone located downstream in the displacement direction of the solid particles from the introduction zone of said solid particles, a stage of contacting said solid particles and said charge in a zone located in the vicinity of the first end, a stage of circulating the solid particles and the charge into the reaction zone and during which said charge is converted and the at least partial deactivation of the catalytic solid particles by the deposition of coke thereof, a stage of at least partial separation containing the products of the at least partial conversion of said charge in a separation zone located in the vicinity of a second end of the reaction zone opposite to said first end, a regeneration stage, in at least one regeneration zone, of at least one part of the solid catalytic particles, which are at least partly deactivated and a stage of recycling the solid catalytic particles, which are at least partly regenerated, in a recycling zone in the vicinity of said first end, characterized in that the separation of the solid particles and the gases containing the products of the reaction is performed in a co-current cyclone separator.

In a special embodiment the co-current cyclone separator comprises at least one introduction means of at least one fluid making it possible to simultaneously strip the solid particles. This fluid is normally a gas chosen from among the gases conventionally used for carrying out such a stripping. This gas will e.g. be steam or an inert gas, such as e.g. nitrogen.

In such a co-current cyclone separator it is possible, contrary to the situation in countercurrent separators, by placing the internal inlet of the light phase L1 (essentially in gaseous form) relatively close to the inlet (at a distance less than the length (Lc) of the countercurrent cyclone separator) for the mixture M1 (containing the solid particles forming a dense phase D1 and the gases forming a light phase L1) and by controlling the circulation of the light phase in the separator, to obtain a rapid separation of the phases, while still maintaining a good effectiveness of the collection of the dense phase D1 and while having an acceptable light phase residence time distribution.

In a preferred embodiment of the present invention use is made of a special co-current cyclone separator making it possible to very rapidly bring about the separation of the dense phase D1 and the light phase L1 from their mixture M1, with a very good effectiveness of collection of the dense phase D1 and a distribution of the residence times of the light phase L1 in said separator narrower than in the prior art cyclone separator. The useful volume for the separation process can, in the special co-current cyclone separator used in the inventive process, be smaller than in the prior art separator and consequently the constant light phase flow separation can be faster.

When used in a preferred embodiment of the invention, said co-current cyclone separator comprises in combination:

at least one external enclosure, elongated along an axis, having a substantially circular section of diameter (Dc) and having at a first end introduction means making it possible to introduce by an external inlet the mixture M1 containing the solid particles forming the dense phase D1 and the gases forming the light phase L1, said means being appropriate to give at least to the said light phase L1 a helical movement in the flow direction of said mixture M1 into said external enclosure, while also comprising means for separating the phases D1 and L1 and at the end opposite to said first and recovery means making it possible to recover by an outlet having a lateral or axial pipe and referred to as the external outlet, at least part of the dense phase D1 and having between said opposite ends a length L, at least one internal enclosure elongated along an axis and having a substantially circular section arranged coaxially with respect to said external enclosure and having at a distance Ls, smaller than L, from the extreme level of the external inlet, a so-called internal inlet having an internal diameter (Di) smaller than (Dc) and which is penetrated by at least part of the light phase L1 and at its opposite end recovery means making it possible to recover by a so-called internal pipe, which is respectively axial if the pipe of the external outlet is lateral, or lateral if the pipe of the external outlet is axial, said part of the light phase L1, said cyclone separator also having downstream, in the circulation direction of the dense phase D1 from the level of the internal inlet of the internal enclosure, means limiting the advance of the light phase L1 outside said internal enclosure.

The invention will be better understood by the description of a number of embodiments given in a purely illustrative and non-limitative manner and with reference to the attached FIGS. 1, 2A, 2B, 3, 4, 5 and 6, in which similar members are designated by the same reference letters and numerals.

BRIEF DESCRIPTION OF THE DRAWINGS

FIG. 1 is a schematic flowsheet of the process of the invention;

FIG. 2A is a perspective view of a vertical cyclone separator in partial cross section having a tangential inlet;

FIG. 2B is a perspective view of a vertical cyclone separator having a different recovery arrangement than FIG. 2A;

Figure 3:
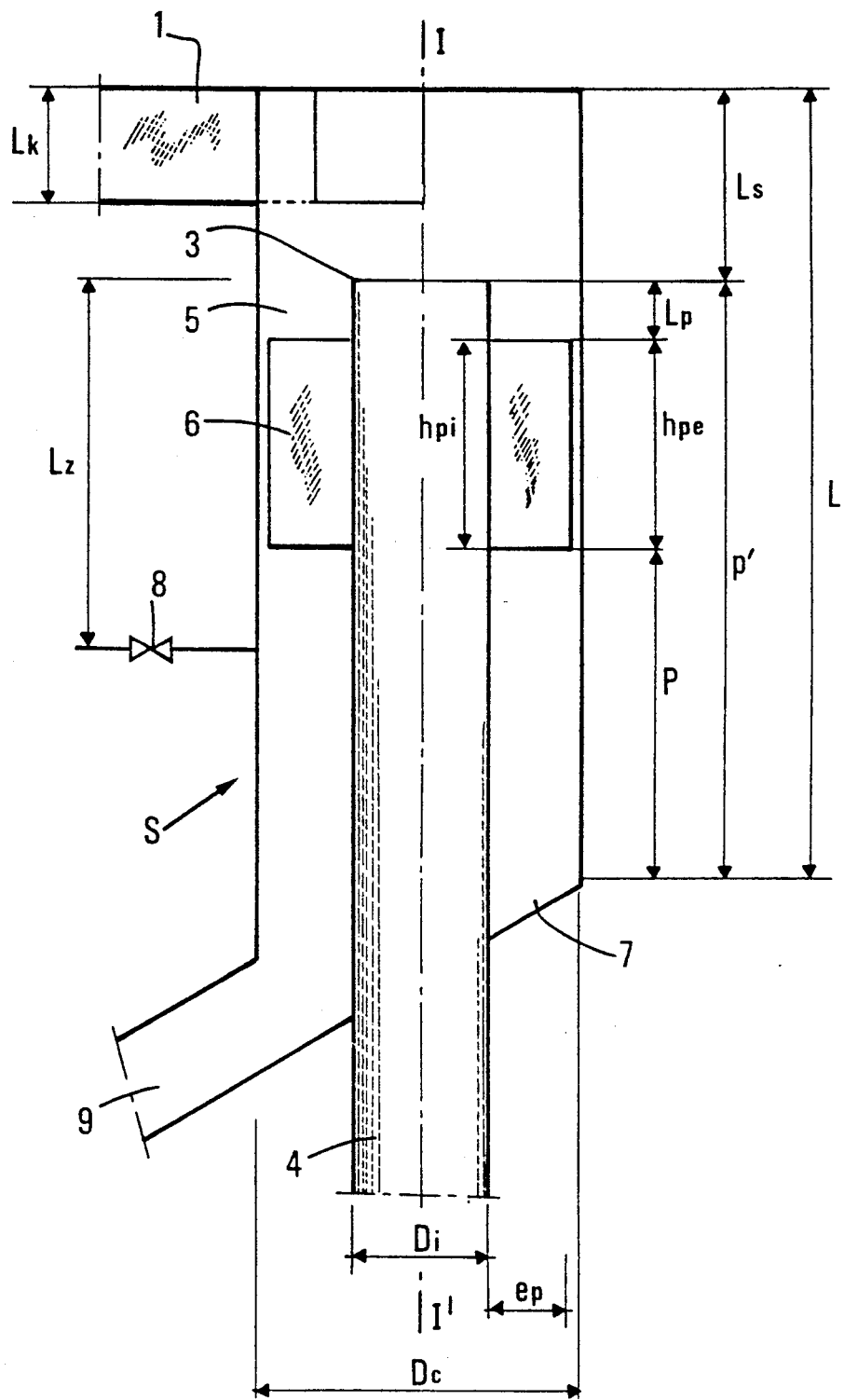
FIG. 3 is primarily a sectional view of FIG. 2B but with additional features.

According to FIG. 1, conversion takes place in a reactor (100), into which the charge is introduced by the pipe (20), the catalytic solid by the pipe (30) and the entrainment gas for the solid by the pipe (40), the reactor being connected by a pipe (1) to a co-current cyclone separator (S) making it possible to separate a solid phase from a gaseous phase containing the conversion products recovered by the pipe (1). The solid phase is supplied by the pipe (9) to a regenerator (R), in which the catalytic particles are at least partly regenerated before being returned by the pipe (80), connected to the pipe (30), to the reactor (100).

FIG. 2A is a perspective view of a co-current cyclone separator used in a preferred embodiment of the invention and referred to hereinafter as the apparatus. FIG. 2B is a perspective view of an apparatus used in the present invention and which only differs from that of FIG. 2A by the recovery means for the dense phase D1 and the light phase L1. In the case of the apparatus shown in FIG. 2B, said means permit a recovery by a lateral pipe of the dense phase D1 and a recovery by an axial pipe of the light phase L1, whereas in the embodiment shown in FIG. 2A it permits a recovery by an axial pipe of the dense phase D1 and a recovery by a lateral pipe of the light phase L1.

FIG. 3 is a sectional view of an apparatus used in the process according to the invention and which is substantially identical to that shown in FIG. 2B, and which shows means (6) limiting the advance of the light phase L1 outside the internal enclosure, whose dimensions in the direction perpendicular to the axis of the external enclosure are smaller than that of the external outlet (5).

The apparatuses used within the scope of the invention and shown in FIGS. 2A and 3 are substantially regular and elongated, incorporating a substantially vertical external enclosure having an axis (I—I'), which is an axis of symmetry, of diameter (Dc) and of length (L) between the extreme level of the tangential inlet (1), referred to as the external inlet, and the discharge means (7) of the dense phase D1. The mixture M1 containing the dense phase D1 and the light phase L1 is introduced by the tangential inlet (1) in a direction substantially perpendicular to the axis of the external enclosure. This tangential inlet preferably has a rectangular or square section, whose side parallel to the axis of the external enclosure has a dimension (Lk) normally approximately 0.25 to approximately once the diameter (Dc) and the side perpendicular to the axis of the external enclosure has a dimension (hk) normally approximately 0.05 to approximately 0.5 times the diameter (Dc).

These apparatuses have an internal enclosure, which is elongated along an axis, which is substantially vertical and has a substantially circular cross-section, positioned coaxially with respect to said external enclosure and having a distance (Ls), less than (L), from the extreme level of the external inlet (1), a so-called internal inlet (3) of diameter (Di) smaller than (Dc). The diameter of said internal inlet (3) is normally approximately 0.2 to approximately 0.9 times the diameter (Dc) and more usually approximately 0.4 to approximately 0.8 times the diameter (Dc) and preferably approximately 0.4 to approximately 0.6 times the diameter (Dc). The distance (Ls) is normally approximately 0.2 to approximately 9.5 times the diameter (Dc) and most usually approximately 0.5 to approximately twice the diameter (Dc). A relatively short distance between 0.5 and twice the diameter (Dc) conventionally permits a very rapid separation, whilst still ensuring a good separation efficiency.

Downstream in the circulation direction of the dense phase D1 from the level of the internal inlet (3), said apparatuses have means (6) limiting the progression or advance of the light phase L1 into the space located between the inner wall of the external enclosure and the outer wall of the internal enclosure or external outlet (5). These means (6) are conventionally positioned within the external enclosure and outside the internal enclosure (between the outer wall of the internal enclosure and the inner wall of the external enclosure), between the level of the internal inlet (3) and the means (7) for recovering the dense phase D1. These means (6) are preferably substantially planar blades, whose plane passes through a substantially vertical axis and which are normally fixed to at least one wall of one of the internal or external enclosures. These means are preferably fixed to the wall of the internal enclosure, so that the distance (Lp) between the internal inlet and the point of said blades closest to said internal inlet is approximately 0 to approximately 5 times the diameter (Dc) and preferably approximately 0.1 to approximately once said diameter (Dc).

The number of blades varies as a function of the residence time distribution accepted for the phase L1 and also as a function of the diameter (Dc) of the external enclosure. The number of blades is normally at least 2 and is e.g. 2 to 50 and most usually 3 to 50. The blades make it possible to limit the continuation of the vortex over the entire cross-section of the cyclone in the external outlet (5), around the pipe forming the internal enclosure and connecting the internal inlet (3) to the internal outlet (4) for the light phase and consequently a reduction and control of the residence time distribution of said phase within the apparatus.

Thus, when using an apparatus of the type described hereinbefore and within the scope of the inventive process, there is a limitation to the residence time of the light phase L1 and the distribution of said residence times and consequently there is a limitation to the deterioration of the products contained in the light phase circulating around the internal inlet.

Each of these blades normally has a dimension or width (ep) measured in the direction perpendicular to the axis of the internal enclosure (i.e. horizontally from its edge closest to the axis of the external enclosure) and defined relative to the internal diameter (Dc) of the external enclosure and the external diameter (D'e) of the internal enclosure of approximately 0.01 to once the value $[((Dc)-(D'e))/2]$ of the half-difference of said diameters (Dc) and (D'e), preferably approximately 0.5 to approximately once said value and more usually approximately 0.9 to approximately once said value.

In the case of a vertical apparatus, used in the process according to the invention and e.g. such as that shown in FIG. 2A, which has a lateral internal outlet (4) and when the blades are positioned after said internal outlet, said dimension (ep) can be approximately 0.01 to approximately once the value (Dc)/2 of the half-diameter of the external enclosure.

These blades have on their edge closest to the internal enclosure axis in the direction parallel to the substantially vertical axis through which passes the plane of the blade, a dimension or internal height (hpi) and a dimension or external height (hpe) measured in the direction parallel to the substantially vertical axis through which passes the plane of the blade, on the edge of said blade closest to the internal wall of the external enclosure. These dimensions (hpi) and (hpe) normally exceed 0.1 times the diameter (Dc) and e.g. represent approximately 0.1 to approximately 10 times the diameter (Dc) and most usually approximately 1 to approximately 4 times said diameter (Dc). Preferably these blades each have a dimension (hpi) equal to or exceeding their dimension (hpe).

According to the embodiment shown in FIGS. 2A and 3, the apparatus has downstream in the flow direction of the different phases from the internal inlet (3), at least one means (8) permitting the possible introduction of a light phase L2 at a point located between the internal inlet (3) of the internal enclosure and the end of the recovery pipe (9) for the dense phase D1. Said point or points are preferably at a distance (Lz) from the internal enclosure inlet (3). Said distance (Lz) preferably has a value at least equal to the sum of the values of (Lp) and (hpi) and at the most equal to the distance between the internal enclosure inlet (3) and the discharge means (7) for the dense phase D1. The light phase L2 can e.g. be introduced in the case where it is desirable to carry out a stripping of the dense phase D1. In this case, said light phase constitutes the stripping fluid. This light phase L2 is preferably introduced at several points, which are normally symmetrically distributed in a plane at the level of which the introduction takes place around the external enclosure.

The introduction point or points of said light phase L2 are normally located at a distance at least equal to 0.1 times the diameter (Dc) of the point of said means (6) closest to the discharge means (7) for the dense phase D1. The introduction point of said light phase L2 is preferably located in the vicinity of the recovery pipe (9) for the dense phase D1 and usually in the vicinity of the discharge means (7) for the dense phase D1.

The dimension (p') between the level of the internal inlet (3) and the discharge means (7) for the dense phase D1 is determined on the basis of other dimensions of various means forming the apparatus and the length (L) of the external enclosure measured between the extreme level of the tangential inlet (1) and the discharge means (7) for the dense phase D1. This dimension (L) is normally approximately 1 to approximately 35 times the diameter (Dc) of the external enclosure and more usually approximately 1 to 25 times said diameter (Dc). In the same way it is possible to calculate the dimension (P) between the point of the means (6) closest to the discharge means (7) for the dense phase D1 and said means (7) on the basis of other dimensions of the various means forming the apparatus and the length (L).

The means (6) limit the advance of the vortex of the light phase L1 into the external outlet (5). The position and number of said means (6) therefore influences the performance characteristics of the separation of the phases D1 and L1 contained in the mixture M1 (pressure drop and efficiency of the collection of the phases) and also the penetration of the vortex of the light phase L1 into the outlet (5). Therefore these parameters will be carefully chosen by the Expert, in particular as a function of the desired results and the acceptable pressure drop. In particular, the number of blades, their shape and their position will be carefully chosen bearing in mind their influence on the flow of the solid, in conjunction with the sought limitation of the advance of the vortex into the external outlet (5).

Figure 4:
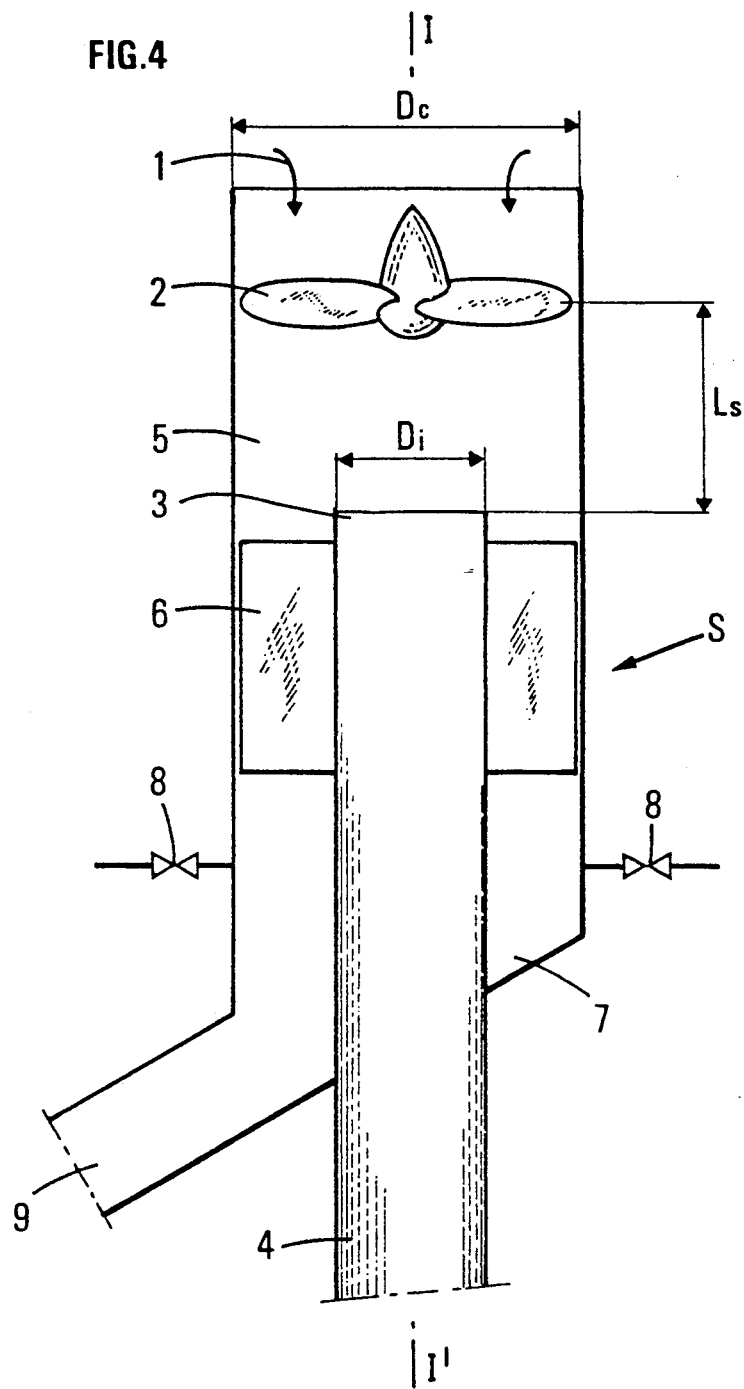
FIG. 4 is a perspective view of another separator having an axial instead of a tangential inlet.

FIG. 4 is a perspective view of an apparatus usable in the process according to the invention and having an external enclosure of diameter (Dc) with a so-called axial external inlet (1), into which is introduced in a direction substantially parallel to the axis (I—I') of the external enclosure, the mixture M1 containing the dense phase D1 and the light phase L1. Said apparatus also has means (2) placed within the inlet (1) making it possible to give downstream, in the circulation direction of said mixture M1, a helical or turbulent movement at least to the phase L1 of said mixture M1. These means are normally inclined blades. The apparatus length L is counted between said means making it possible to create a vortex at least with respect to the phase L1 and the discharge means (7) for the dense phase D1. All the other characteristics are identical to those described in conjunction with the apparatuses shown in FIGS. 2A and 3 and in particular the various dimensions are those given in connection with the description thereof. The variants described in conjunction with the apparatuses shown in FIGS. 2A and 3 are also possible in the case of the apparatus shown in FIG. 4. It is in particular possible to envisage a lateral internal outlet (4) and an axial recovery pipe (9) for the dense phase D1, as in the case shown in FIG. 2B.

Figure 5:
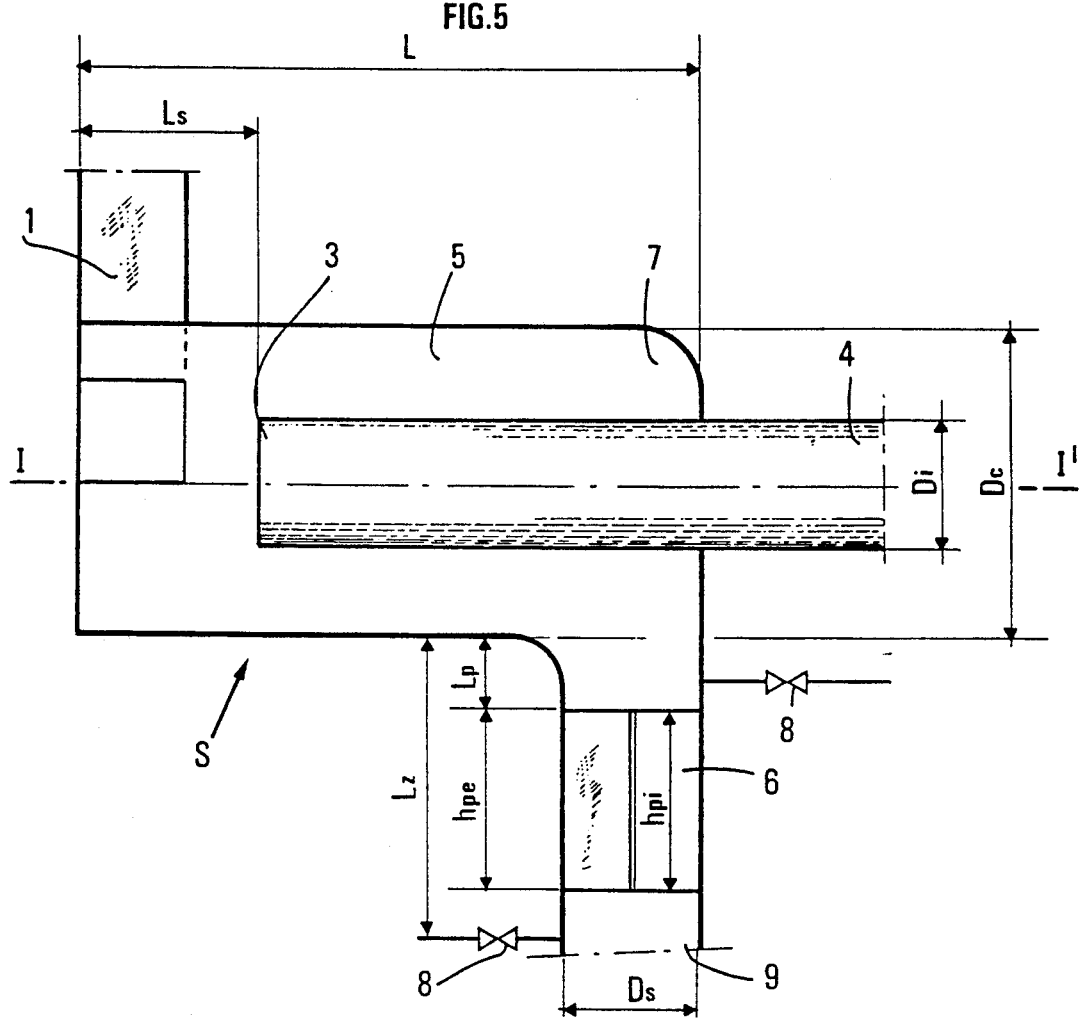
FIG. 5 is a perspective view in partial cross section of a horizontal separator.

FIG. 5 is a sectional view of an apparatus usable in the process of the invention, which is elongated and substantially regular and has an external enclosure with an axis (AA'), which is an axis of symmetry and substantially horizontal, of diameter (Dc) and length (L) between the extreme level of the tangential or external inlet (1) and the discharge means (7) for the dense phase D1. The mixture M1 containing the dense phase D1 and the light phase L1 is introduced by the tangential inlet (1) in accordance with a direction substantially perpendicular to the axis of the external enclosure.

This apparatus also has, downstream in the circulation direction of the dense phase D1 from the internal inlet (3), means (6) limiting the advance of the light phase L1, outside the internal enclosure, into the space located between the inner wall of the external enclosure and the outer wall of the internal enclosure or external outlet (5). These means (6) are normally positioned downstream in the flow direction of the dense phase D1, of the recovery means (7) for the dense phase D1 in the recovery pipe (9) for the dense phase D1 of diameter (Ds).

These means (6) are normally substantially planar blades, whose plane passes through a substantially vertical axis. The dimension (ep) of each of these blades is normally approximately 0.01 to approximately once the diameter (Ds) of the pipe (9). The blades are normally positioned in such a way that the internal edge, i.e. the edge of the blade closest to the axis of the pipe (9), of each of them, coincides with the axis of said pipe (9). These blades are positioned at a distance (Lp) relative to the separation means (7) of approximately 0 to approximately 5×(Dc).

The means (8) making it possible to optionally introduce the light phase L2 are normally positioned downstream, in the flow direction of the dense phase D1, from the level of the internal inlet (3) and preferably between the recovery means (7) of the dense phase D1 and the end of the recovery pipe (9) for said dense phase D1. In the case of the apparatus shown in FIG. 5, the light phase L2 is introduced at two different levels by a first means (8) level with the means (7) and by a second means (8) positioned below the means (6). The means (8) are positioned at a distance (Lz) from the recovery means of the dense phase D1 and measured as from the said means (7). The apparatus shown in FIG. 5 has a pipe (9) for the recovery of the dense phase D1, having a diameter (Ds) normally equal to approximately 0.1 to approximately once the diameter (Dc) and usually approximately 0.2 to approximately 0.7 times said diameter. All the other characteristics of this horizontal cyclone separator are identical to those described in conjunction with the apparatuses shown in FIGS. 2A and 3 and in particular the various dimensions are as indicated in the description of said apparatuses.

Although not shown in FIGS. 2A, 2B3, 4 and 5, it is possible and normally desirable, in the case of high flow rates for the different phases at the apparatus inlets, to use means making it possible to aid the formation of the vortex. Such means (10) are e.g. shown in FIG. 6, which shows in a preferred embodiment of the apparatus used in the inventive process, the adjacent part of the tangential inlet (1) with respect to the mixture M1. The apparatus has an e.g. helical roof or top (10) dropping from the extreme level of the tangential inlet (1). These means (10) can also consist of an internal or external helix. These means also make it possible to limit interference between the flow of the mixture M1 and the flows of the phases already present in the separator and also limit the turbulence at the tangential inlet (1). Normally and in particular in the case of a downward helical top, the pitch of the helix is approximately 0.01 to approximately 3 times the value of (Lk) and most usually approximately 0.5 to approximately 1.5 times said value.

Figure 6:
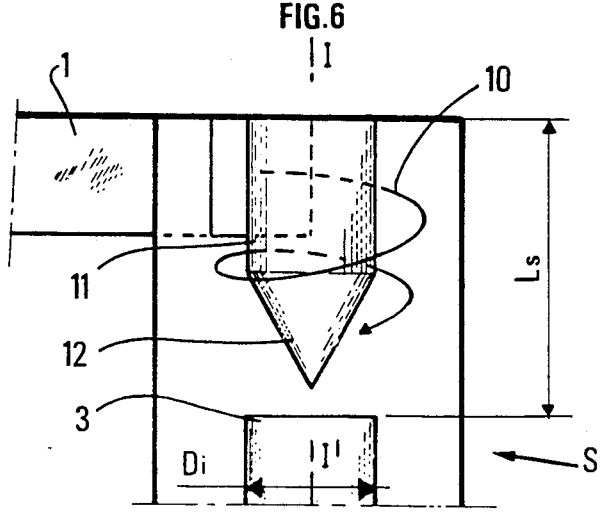
FIG. 6 is a partial cross showing helical means for forming a vortex.

In this preferred form of the apparatus used in the inventive process, it also has between the external inlet and the internal inlet, means for stabilizing the helical flow of at least the light phase L1 and for limiting the separation-useful volume. These means are preferably centered on the axis of the internal enclosure. These means can be a cone, whose apex is directed towards the internal inlet and whose base is at the extreme level of the tangential inlet (1). As shown in FIG. 6, they can also be formed by a cylinder (11) extended by a cone (12). The diameter of the base of the cone is identical to that of the cylinder and is well below the diameter (Dc). This diameter is normally approximately 0.01 to approximately 1.5 times the diameter (Di) of the internal inlet (3) and preferably approximately 0.75 to approximately 1.25 times the diameter (Di). The axial dimension or size between the extreme level of said means closest to the tangential inlet and the opposite end of said means is normally approximately 0.01 to approximately 3 times the value (Ls) of the distance between the extreme level of the tangential inlet (1) and the level of the internal inlet (3) and is preferably approximately 0.75 to approximately 1.25 times said value (Ls).

The discharge means (7) for the dense phase D1 normally make it possible to collect and channel said dense phase D1 up to the external outlet (9). These means are normally an inclined base or bottom or a cone, which may or may not be axed on the internal outlet (4).

The apparatuses described hereinbefore and used in the process according to the invention, thus permit a rapid separation from a mixture M1, incorporating a dense phase and a light phase, of said dense phase and said light phase.

The diameter (Dc) of the apparatus measured at the tangential inlet (1) on the side of its end closest to the internal inlet (3) is normally approximately 0.01 to approximately 10 m and usually approximately 0.05 to approximately 2 m. It is normally preferable to maintain a constant diameter over the entire length of the apparatus between the end of the tangential inlet closest to the internal inlet (3) and said internal inlet (3), or even from the injection level of the mixture M1 to the level of the discharge means (7) for the dense phase D1. However, it is possible to envisage the construction and use of an apparatus having cross-sectional narrowings and widenings between the said levels.

In order to obtain a good separation of the light phase L1 contained in the mixture M1 also incorporating the dense phase D1, it is preferable to have a high surface intake velocity or speed for said phase L1 and which is e.g. approximately 0.1 to approximately 250 mxs−1 (meters per second) and preferably approximately 0.5 to approximately 75 mxs−1 and most usually approximately 1 to 20 mxs−1. The weight ratio of the flow rate of the phase D1 to the flow rate of the phase L1 is normally approximately 2:1 to approximately 100:1 and most usually approximately 5:1 to approximately 50:1. By increasing the pressure difference between the inlet (3) and the means (7), which can e.g. be brought about by increasing the pressure downstream in the flow direction of the dense phase D1 from the internal inlet (3) or by decreasing the downstream pressure in the flow direction of the dense phase D1 from the discharge means (7) for said phase, it is possible to draw off a varying proportion of the phase L1 with the phase D1 and simultaneously obtain at the outlet (4) a mixture substantially completely free from phase D1. It is thus possible to e.g. draw off approximately 1 to approximately 10% of the phase L1 with D1. The pressure variations making it possible to act on the quantity of phase L1 drawn off with the phase D1 are ensured by known means and e.g. by modifying the flow rate of the phase L2, or by modifying the operating conditions downstream of the outlet (9). Thus, in a special embodiment of the invention, the apparatus has at least one means permitting the drawing off, through the external outlet (5), of at least part of the light phase L1 mixed with the dense phase D1.

In the apparatuses used in the process according to the invention and in the different injection modes of the mixture M1, such a drawing off can make it possible to improve the recovery efficiency of the dense phase D1. The choice between an apparatus having a tangential inlet for the mixture M1 and an apparatus having an axial inlet for said mixture M1 is normally guided by the weight ratio of the flow rates of phases L1 and D1. When this ratio is below 5:1, it can be advantageous to choose an apparatus with an axial inlet.

The present invention also relates to an apparatus for the entrained bed catalytic conversion of a charge containing at least one oxygen compound into olefinic hydrocarbons rich in compounds having 2 to 4 carbon atoms in their molecule, having an elongated enclosure in which said conversion takes place under appropriate conditions and having, in the vicinity of a first end, upstream and downstream in the displacement direction of the charge, at least one means for introducing at least one entrainment fluid, at least one means for introducing at least one solid containing catalytic particles, at least one means for introducing said charge, the apparatus having in the vicinity of a second end of said closure at least one means, connected to the said enclosure, for separating solid particles and gases containing the products of the at least partial conversion of said charge and at least one means for regenerating at least part of the solid catalytic particles connected on the one hand to the separation means for said solid particles and on the other to the said enclosure in the vicinity of said first end, so as to permit the regeneration of at least part of the solid catalytic particles and the recycling of said solid particles into said enclosure, characterized in that said means for separating the solid particles and gases is a co-current cyclone separator. The apparatus preferably comprises a co-current cyclone separator having at least one means for introducing at least one stripping fluid.

The co-current cyclone separator used in preferred manner comprises in combination:

at least one external enclosure, elongated along an axis and having a substantially circular cross-section of diameter (Dc), having at a first end introduction means making it possible to introduce, by a so-called external inlet, the mixture M1 containing the solid particles forming the dense phase D1 and the gases forming the light phase L1, said means being able to give at least to the light phase L1 a helical movement in the flow direction of said mixture M1 into said external enclosure, also having means for separating the phases D1 and L1 and at the end opposite to said first end recovery means permitting the recovery by an outlet, which has a lateral or axial pipe and which is referred to as the external outlet, of at least part of the dense phase D1 and having between said opposite ends a length L, at least one internal enclosure of elongated shape along an axis and having a substantially circular cross-section, positioned coaxially with respect to said external enclosure and having a distance Ls, smaller than L, from the extreme end of the external inlet, a so-called internal inlet having a diameter (Di) smaller than (Dc), which is penetrated at least partly by the light phase L1 and at its opposite end recovery means making it possible to recover, by a so-called internal pipe, which is respectively axial if the pipe of the external outlet is lateral, or lateral if the pipe of the external outlet is axial, said part of the light phase L1, said cyclone separator having downstream, in the flow direction of the dense phase D1 from the internal inlet of the internal enclosure, means limiting the advance of the light phase L1 outside said internal enclosure.

Within the scope of the present invention no reference has been made to the solids and catalysts used, or to the various fluids used, which are of a conventional nature with respect to the catalyst conversion of oxygen or oxygen-containing compounds into olefinic hydrocarbons. The entrainment fluid is usually chosen from within the group formed by steam, inert gases or gaseous hydrocarbons, or mixtures of these compounds. The reaction performance conditions are often those used in an entrained fluidized bed. In this case the fluidization fluid is usually the same as the entrainment fluid. This single fluid is then subdivided into two fractions, one forming the fluidization fluid and the other the entrainment fluid. The catalysts used are preferably zeolitic catalysts.

The operating conditions with respect to the conversion processes of the oxygen-containing charges, such as methanol, are e.g. those described in U.S. Pat. Nos. 4,689,205, 3,969,426 and 4,229,608, but none of these patents describes the use of a co-current cyclone separator for improving the speed of solid-gas separation.

The operating conditions for converting the oxygen-containing charge are generally as follows: The charge, which usually contains an alcohol and normally methanol, generally contains 50 to 100, preferably 70 to 90% by weight of the oxygen-containing compounds and 0 to 50 and preferably 5 to 30% by weight water. The charge can also contain an inert gas, such as e.g. nitrogen alone or mixed with steam in the proportion indicated hereinbefore for the steam. In the most frequent case where the charge contains methanol, it can be constituted by crude methanol, such as that obtained from a unit for synthesizing this compound from a gas containing carbon monoxide. The injection temperature is normally the same as the dew point of the charge. The absolute pressure in the conversion unit is usually 0.1 to 0.5 megapascal (MPa) and most frequently approximately 0.2 MPa. The temperature of the reaction zone is usually 500° to 620° C. and most frequently 550° to 590° C. The residence time in the reaction zone is normally 0.05 to 10 seconds and most frequently 0.5 to 3 seconds. The velocity of the gases in the reaction zone is normally 0.5 to 40 m/s and most frequently 1 to 20 m/s. The velocity of the solids in the reaction zone is normally close to that of the gases and is generally 0.5 to 40 m/s and most frequently 1 to 20 m/s.

The operating conditions are chosen in such a way that the composition of the products obtained, expressed by the carbon yield of ethylene compounds having 2 to 4 carbon atoms in their molecule exceeds 70% and preferably exceeds 80%. The products obtained can be particularly rich in ethylene (carbon yield for ethylene exceeding 40%) or particularly rich in propylene (carbon yield for propylene exceeding 60%). The density of the solids is usually 10 to 700 kg/m$^3$ and usually 20 to 400 kg/m$^3$. The C/O ratio of the mass flow rate of the catalyst to the mass flow rate of the charge is normally approximately 2:1 to approximately 50:1 and most frequently approximately 5:1 to approximately 30:1.

We claim:

1. In an entrained bed process for the catalytic conversion of a change containing at least one oxygen compound into olefinic hydrocarbons rich in compounds having 2 to 4 carbon atoms in their molecule, the steps comprising:

supplying, to a zone located in the vicinity of a first end of an elongated reaction zone, catalytic solid particles and at least one entrainment fluid so as to establish an entrained bed;

contacting said catalytic solid particles and said charge in a zone located in the vicinity of the first end;

circulating the solid particles and the charge in the reaction zone to at least partially convert said charge and to at least partially deactivate the catalytic solid particles by the deposition of coke thereon;

withdrawing from a second end of said elongated reaction zone a mixture M1 containing products of the at least partial conversion of said charge and at least partially separating said mixture M1;

regenerating at least one part of the deactivated solid catalytic particles; and recycling resultant at least partially regenerated solid catalytic particles to a recycling zone in the vicinity of said first end, the improvement which comprises:

conducting the separation of the solid particles and the gases containing the products of the reaction in the mixture M1 in a co-current cyclone separator comprising at least one external enclosure, elongated along an axis, having a substantially circular section of diameter (Dc) and having at a first end introduction means;

introducing by an external inlet the mixture M1 containing the catalytic solid particles forming a dense phase D1 and the charge in a gaseous form forming a light phase L1 and imparting at least to the said light phase L1 in said external enclosure a helical movement in the flow direction of said mixture M1 and separating the phases D1 and L1, and recovering at the second end opposite said first end via an external outlet, at least part of the dense phase D1, said external enclosure having between said opposite ends a length L;

at least one internal enclosure elongated along an axis and having a substantially circular section arranged coaxially with respect to said external enclosure and having at a distance Ls, smaller than L, from the extreme level of the external inlet, an internal inlet having an internal diameter (Di) smaller than (Dc); and passing through said internal enclosure at least part of the light phase L1 to an opposite end of the internal inlet and recovering the at least part of the light phase L1 by an internal pipe, which is respectively axial when the pipe of the external outlet is lateral, or lateral when the pipe of the external outlet is axial, said cyclone separator also having downstream, in the circulation direction of the dense phase D1 means limiting the advance of the light phase L1 outside said internal enclosure.

2. A process according to claim 1, further comprising introducing into the co-current cyclone separator at least one fluid so as to strip the solid particles.

3. A process according to claim 2, wherein the external enclosure is substantially vertical and the means limiting the advance of the light phase L1 to the outside of the internal enclosure are positioned within the external enclosure and outside the internal enclosure, between the level of the internal inlet and the recovery means for the dense phase D1.

4. A process according to claim 2, wherein the external enclosure is substantially horizontal and the means limiting the advance of the light phase L1 to the outside of the internal enclosure are positioned, downstream, in the flow direction of the dense phase D1, of the recovery means for said dense phase D1, in the external outlet pipe.

5. A process according to claim 2, wherein the means limiting the advance of the light phase L1 to the exterior of the internal enclosure are substantially planar blades, whose plane passes through a substantially vertical axis.

6. A process according to claim 5, wherein the cyclone separator has 2 to 50 blades each having a dimension (ep), measured horizontally, from its edge closest to the axis of the external enclosure approximately 0.01 to approximately once the value $[((Dc)-(D'e))/2]$ when these blades are, in the case of a vertical cyclone separator, positioned between the outer wall of the internal enclosure of external diameter (D'e) and the inner wall of the external enclosure of internal diameter (Dc), of approximately 0.01 to approximately once the value (Dc)/2 in the case of a vertical cyclone separator at the lateral internal outlet, when they are positioned after said internal outlet and approximately 0.01 to once the diameter (Dc) of the external discharge pipe in the case of a horizontal cyclone separator, a dimension (hpe), measured in the direction parallel to the substantially vertical axis through which passes the plane of the blade, on the edge of the blade closest to the inner wall of the external enclosure or the inner wall of the external outlet and a dimension (hpi) measured, on the edge of the blade closest to the axis of the internal enclosure or the axis of the external outlet, in the direction parallel to the substantially vertical axis through which passes the plane of the blade, said dimensions (hpe) and (hpi)

being approximately 0.1×(Dc) to approximately 10×(Dc) and said blades being in each case located at a distance, relative to the internal inlet in the case of a vertical cyclone separator, or relative to the separating means in the case of a horizontal cyclone separator, of approximately 0 to approximately 5×(Dc).

7. A process according to claim 6, wherein each of the blades has a dimension (hpi) equal to or exceeding (hpe).

8. A process according to claim 1 wherein the introduction means of at least one fluid constituting a light phase L2 making it possible to carry out simultaneously the stripping of the solid particles is positioned between the internal inlet of the internal enclosure and the end of the external discharge pipe of the cyclone separator.

9. A process according to claim 2, wherein the cyclone separator has between the external inlet and the internal inlet, means for stabilizing the helical flow of at least the light phase L1 and for limiting the separation-useful volume.

10. A process according to claim 2, wherein the mixture M1 is introduced in a direction substantially parallel to the axis of the external enclosure or in a direction substantially perpendicular to the axis of the external enclosure.

11. A process according to claim 2, wherein the cyclone separator comprises means for limiting interference between the flow of the mixture M1 introduced and the flow of the phases already present in the separator and chosen from among a descending top, an external helix and an internal helix.

12. A process according to claim 1, wherein the charge comprises at least one alcohol, and wherein it is introduced in the gaseous phase.

13. A process according to claim 1, wherein the co-current cyclone separator has at least one means for introducing at least one fluid making it possible to strip the solid particles.

14. A process according to claim 3, wherein the means limiting the advance of the light phase L1 to the exterior of the internal enclosure are substantially planar blades, whose plane passes through a substantially vertical axis.

15. A process according to claim 4, wherein the means limiting the advance of the light phase L1 to the exterior of the internal enclosure are substantially planar blades, whose plane passes through a substantially vertical axis.

16. A process according to claim 12, wherein said at least one alcohol is methanol.

* * * * *